(12) United States Patent
Wright et al.

(10) Patent No.: US 7,942,823 B2
(45) Date of Patent: May 17, 2011

(54) METHODS AND APPARATUS FOR STROKE PATIENT TREATMENT

(75) Inventors: Jonathan Caldwell Wright, Clontarf (AU); Anthony John Ujhazy, East Lindfield (AU); Alison Mary Hansford, Canada Bay (AU)

(73) Assignee: Resmed Limited, New South Wales (AU)

( * ) Notice: Subject to any disclaimer, the term of this patent is extended or adjusted under 35 U.S.C. 154(b) by 1475 days.

(21) Appl. No.: 11/339,908

(22) Filed: Jan. 25, 2006

(65) Prior Publication Data

US 2006/0135878 A1      Jun. 22, 2006

Related U.S. Application Data

(63) Continuation of application No. 10/450,068, filed as application No. PCT/AU01/01595 on Dec. 11, 2001, now Pat. No. 7,018,341.

(60) Provisional application No. 60/254,151, filed on Dec. 11, 2000.

(51) Int. Cl.
*A61B 5/08* (2006.01)

(52) U.S. Cl. ... 600/538; 600/529; 600/484; 128/204.23; 128/204.18

(58) Field of Classification Search .......... 600/529–543, 600/484; 128/204.18, 204.21, 204.23
See application file for complete search history.

(56) References Cited

U.S. PATENT DOCUMENTS

| | | | |
|---|---|---|---|
| 3,911,903 A | 10/1975 | Gee et al. | |
| 4,944,310 A | 7/1990 | Sullivan | |
| 5,678,539 A * | 10/1997 | Schubert et al. | 128/204.21 |
| 5,704,345 A | 1/1998 | Berthon-Jones | |
| 6,045,514 A * | 4/2000 | Raviv et al. | 600/529 |
| 6,152,129 A | 11/2000 | Berthon-Jones | |
| 6,322,514 B1 * | 11/2001 | Holte | 600/481 |
| 6,336,454 B1 * | 1/2002 | Farrell et al. | 128/200.24 |
| 6,336,903 B1 * | 1/2002 | Bardy | 600/508 |
| 6,398,728 B1 | 6/2002 | Bardy | |
| 6,484,719 B1 * | 11/2002 | Berthon-Jones | 128/204.23 |

(Continued)

FOREIGN PATENT DOCUMENTS

EP     0 651 971     5/1995

(Continued)

OTHER PUBLICATIONS

PCT International Search Report, PCT/AU01/01595; dated Feb. 5, 2002; Applicant: ResMed Ltd et al.

(Continued)

*Primary Examiner* — Charles A Marmor, II
*Assistant Examiner* — Navin Natnithithadha
(74) *Attorney, Agent, or Firm* — Gottlieb Rackman & Reisman, PC

(57) ABSTRACT

Methods and apparatus for assessing the condition of and treating patients for stroke during the delivery of continuous positive airway pressure (CPAP) are disclosed. By determining central and obstructive apnea occurrences or the percentile of pressure delivered to the patient from patient airflow, stroke indicators may be calculated and analyzed to provide information on the type of stroke a patient has suffered and the degree of a patient's neuro-recovery. The apparatus may be programmed with a particular protocol intended to identify between alternative forms of CPAP treatment appropriate for the patient based upon an assessment of the patient's condition. The device can select and recommend between the various treatment forms, identify billing reimbursement codes and generate data to track patient response to stroke treatments.

17 Claims, 7 Drawing Sheets

U.S. PATENT DOCUMENTS

| | | | |
|---|---|---|---|
| 6,532,957 B2 * | 3/2003 | Berthon-Jones | 128/204.21 |
| 6,532,959 B1 * | 3/2003 | Berthon-Jones | 128/204.23 |
| 6,564,797 B1 | 5/2003 | Mechlenburg et al. | |
| 6,575,163 B1 * | 6/2003 | Berthon-Jones | 128/204.18 |
| 6,600,949 B1 * | 7/2003 | Turcott | 600/518 |
| 6,752,151 B2 * | 6/2004 | Hill | 128/204.18 |
| 6,832,609 B2 * | 12/2004 | Wright et al. | 128/204.23 |
| 7,018,341 B2 * | 3/2006 | Wright et al. | 600/538 |
| 7,267,122 B2 * | 9/2007 | Hill | 128/204.23 |
| 7,636,600 B1 * | 12/2009 | Koh | 607/42 |
| 2002/0185130 A1 * | 12/2002 | Wright et al. | 128/204.21 |
| 2004/0138576 A1 * | 7/2004 | Wright et al. | 600/533 |
| 2006/0135878 A1 * | 6/2006 | Wright et al. | 600/538 |

FOREIGN PATENT DOCUMENTS

| | | |
|---|---|---|
| WO | 98/06449 | 2/1998 |
| WO | WO 98/50095 | 11/1998 |
| WO | WO 98/51362 | 11/1998 |
| WO | WO 98/52467 | 11/1998 |
| WO | WO 99/61088 | 12/1999 |
| WO | WO 01/19433 | 3/2000 |
| WO | WO 00/37135 | 6/2000 |

OTHER PUBLICATIONS

Dyken, ME, Investigating the Relationship Between Stroke and Obstructive Sleep Apnea, Stroke, abstract (Mar. 1996).

Sleep Apnea in Patients with Transient Ischemic Attack & Stroke—A Prospective Study of 59 Patients; Claudio Bassetti et al; c1996 by the American Academy of Neurology; pp. 1167-1173.

Investigating the Relationship Between Stroke & Obstructive Sleep Apnea; Mark E. Dyken et al; c1996 by the American Heart Association Inc; pp. 401-407.

Sleep-Disordered Breathing & Poor Functional Outcome After Stroke; David C Good et al; c1996 by the American Heart Association Inc; pp. 252-259.

Cheyne-Stokes Respiration in Ischemic Stroke; A Nachtmann et al; published Apr. 1995; Neurology 45-Brief Communications; pp. 820-821.

Implementing a Protocol for Using Continuous Positive Airway Pressure for Patients with Stroke; Lisa Schirrick et al; Rehabilitation Nursing; vol. 30, No. 3; May/Jun. 1995; pp. 169-170.

Parra, Olga, Arboix, Adria, Sirei, Bechich, Barcia-Eroles, Luis, Montserrat, Josep M, Lopez, Josep Antoni, Ballester, Eugeni, Guerra, Josep M, Sopena, Juan Jose—"Time Course of Sleep-related Breathing Disorders in First-EVer Stroke or Transient Ischemic Attack"—American Journal of Respiratory and Critical Care Medicine 2000, vol. 161, pp. 375-380.

Ayappa et al, "Cardiogenic Oscillations on the Airflow Signal During Continous Positive Airway Pressure as a Marker of Central Apnea", CHEST, American College of Chest Physicians Sep. 1, 1999; vol. 116; No. 3; pp. 660-666; XP008104298.

* cited by examiner

Rehab Clinic Supports in-patients portable studies

Rehab Clinic establishes/uses full PSG sleep lab

Sleep study conducted at sleep lab after discharge

Sleep study conducted at sleep lab prior to rehab

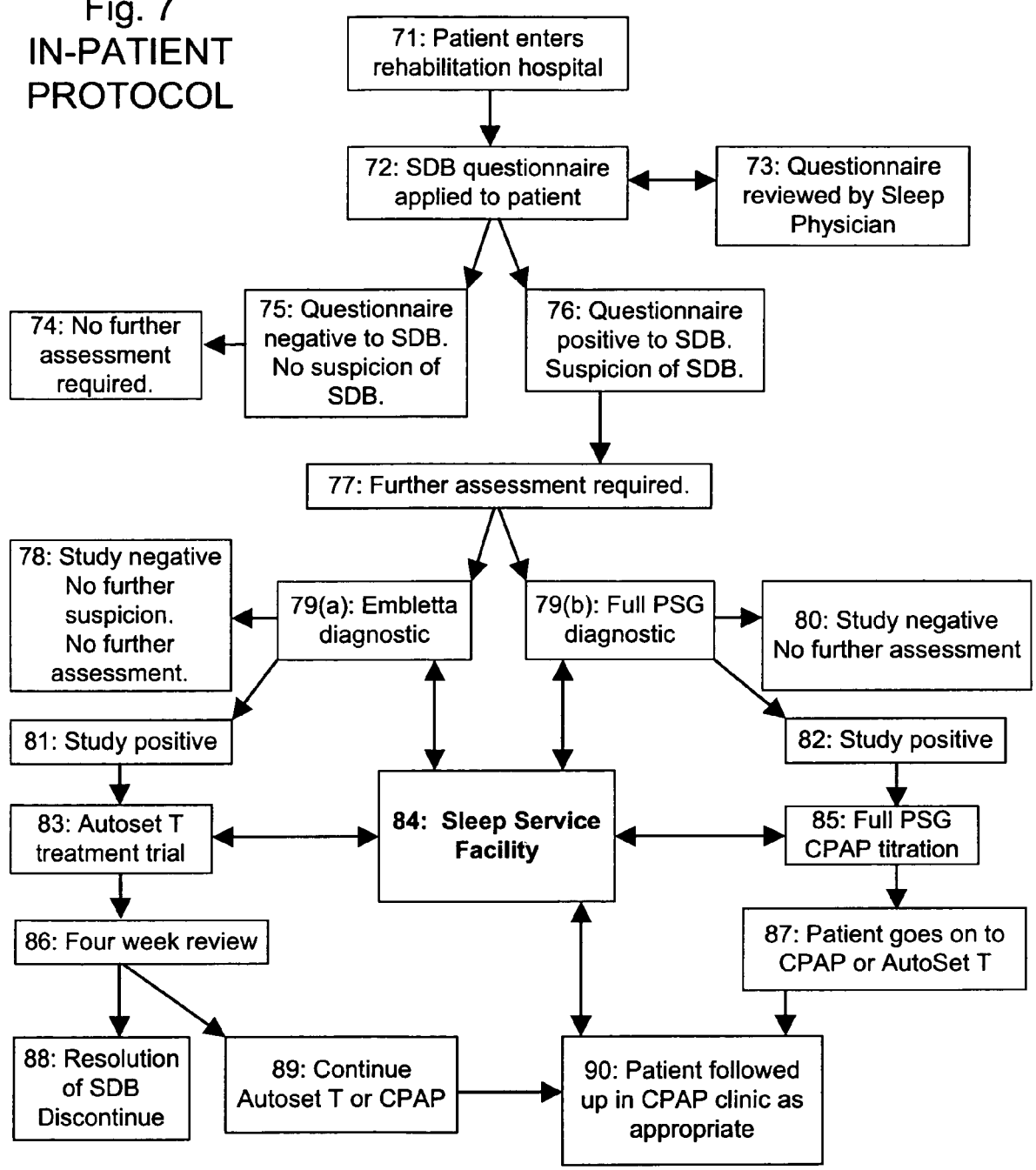

US 7,942,823 B2

METHODS AND APPARATUS FOR STROKE PATIENT TREATMENT

This application is a continuation of application Ser. No. 10/450,068 filed on Dec. 16, 2003 now U.S. Pat. No. 7,018,341, now allowed, which is a National Stage Application of International Patent Application No. PCT/AU01/01595 filed on Dec. 11, 2001, which claims the priority filing date of U.S. Provisional Patent Application Ser. No. 60/254,151 filed on Dec. 11, 2000. U.S. application Ser. No. 10/014,684 filed Dec. 11, 2001, now U.S. Pat. No. 6,832,609, also claims priority of Provisional Application No. 60/254,151.

FIELD OF THE INVENTION

The invention relates to methods and apparatus for diagnosing, managing and treating stroke patients both as in-patients and out-patients.

BACKGROUND OF THE INVENTION

Stroke, or brain attack as it is commonly called, can be caused by either vascular hemorrhage or vascular blockage with the latter accounting for about 80% of the events which lead to a stroke. Vascular hemorrhage is also termed a haemorrhagic stroke or an aneurism. Vascular blockage may also be termed ischaemic stroke. Both types of stroke are associated with considerable morbidity in terms of long-term neurological deficit and the risk of subsequent stroke as well as mortality post stroke.

Stroke treatment in the acute phase typically entails the invasive administration of clot dissolving drugs within the first three hours of the stroke as well as stabilization of cardiovascular functions and vital signs. After treatment in the acute phase, patients may typically follow four pathways: (i) in the case of mild stroke the patient may go home, (ii) in the case of a more severe stroke where it is believed an improvement in outcome can occur the patient may be sent to rehabilitation, (iii) other patients may be sent to special care/nursing home, (iv) some patients die. The present application is concerned with patients in the rehabilitation pathway. Rehabilitation is costly for health care systems hence it is desirable to provide improved patient outcomes at a lower cost where possible.

While the use of a blood thinning agent such as Tissue Plasminogen Activator may be used in the treatment of ischaemic stroke, it may be the wrong therapy to give in the case of a haemorrhagic stroke. Hence it is important to determine the type of stroke which has occurred in the patient. Furthermore, the drug therapy may vary during the course of treatment depending on the progress which the patient makes. Hence it is important to monitor the progress of the patient during treatment.

The application of nasal Continuous Positive Airway Pressure ("CPAP") as a treatment for Obstructive Sleep Apnea ("OSA") was invented by Sullivan and taught in U.S. Pat. No. 4,944,310. That patent described continuous positive airway pressure being applied to a patient, through the patient's nares, to treat breathing disorders, including sleep apnea. It has been found that the application of pressure which exceeds atmospheric pressure, typically in the range 4 to 15 centimeters of $H_2O$ is useful in treatment. OSA is an example of a broader class of breathing disorders generally referred to as Sleep Disordered Breathing ("SDB").

In one form, nasal CPAP treatment of OSA involves the use of a computer controlled blower, such as the AUTOSET T™ device available from ResMed Ltd., to provide a supply of air or breathable gas at pressures in the range of 4 to 20 cm $H_2O$ to the airway of a patient via a mask. Examples of suitable nasal CPAP masks are the MIRAGE™ nasal mask and the MIRAGE™ full face mask also available from ResMed Ltd. The AUTOSET T™ device continuously monitors the state of the patient's airway and determines an appropriate pressure to treat the patient, increasing it or decreasing it as necessary. Some of the principles behind the operation of the AUTOSET T™ device are described in U.S. Pat. No. 5,704,345.

Another form of treatment for SDB is bi-level pressure support ventilation provided by way of a nasal CPAP mask. The treatment involves providing air at a higher pressure during the inspiratory portion of the breathing cycle and at a lower pressure during the expiratory portion of the breathing cycle. A suitable device for delivering bi-level nasal CPAP is the VPAP™ II ST/A available from ResMed Ltd.

A typical clinical pathway for OSA is as follows:
  (i) A patient consults their general practitioner or physician;
  (ii) The general practitioner or physician refers the patient to a specialist or a sleep clinic;
  (iii) The specialist or clinic assesses the patient;
  (iv) An overnight polysomnography is performed;
  (v) An overnight titration study is performed.

In a hospital setting, the team of physicians treating inpatients for other conditions may recognize symptoms of sleep disordered breathing on an ad hoc basis and refer the inpatient to a sleep specialist within the hospital. The patient will then proceed through steps (iii) to (v) as above.

Recently it has become recognized that stroke patients may benefit from treatment with CPAP, for example as taught in International Patent Application WO98/51362 (Farrell & Pace). While the clinical pathways for identifying patients with OSA are becoming more established, there are few clinical pathways for identifying stroke patients who may benefit from such therapies. Furthermore, there are no known devices for managing the therapy of such patients.

It is an objective of the invention to provide methods and apparatus for managing the treatment of respiratory disorders in stroke patients. It is a further objective to provide methods and apparatus which assist in the identification or diagnosis of stroke patient condition to assist in treatment of the patient.

SUMMARY OF THE INVENTION

The invention provides methods and apparatus for managing ventilatory treatment of stroke patients. In one form, the invention provides apparatus for diagnosis, patient monitoring, nasal ventilation, with or without concomitant drug therapy, using continuous positive airway pressure (CPAP) or bi-level pressure treatment or variants thereof, including devices which automatically set their pressures based on physiologic data inputs.

BRIEF DESCRIPTION OF DRAWINGS

FIG. 7 shows a flow chart in accordance with an embodiment of the invention.

DESCRIPTION OF THE INVENTION

Nasal CPAP treatment has been traditionally used for the management of patients with obstructive sleep apnea where CPAP acts as a pneumatic splint to maintain upper airway patency and therefore ensures free flow of air while the patient sleeps. The current invention describes the use of positive pressure ventilation, which may include CPAP, bi-level pressure, or variants thereof, for stroke patients. The use of CPAP treats stroke patients by improving arterial blood oxygenation levels and reducing arterial carbon dioxide levels as well as improving auto-regulation of, for example, blood pressure, cardiac output and ventilation. Improvements in morbidity, such as rate and degree of recovery of vital signs and patient stabilization in the acute phase, is an expected benefit. Also, an improvement in neurological deficits in the short and/or long term is an expected benefit.

The advantages of the use of CPAP in assisting stroke rehabilitation are greater than that provided by oxygenation per se. For example, providing oxygen will in itself not prevent the patient from having an apnea. Reducing or eliminating apneas may reduce the damaging side-effects of apnea, such as unnecessary activation of the sympathetic nervous system, surging blood pressure and increases in blood flow. Furthermore, some CPAP devices can detect the presence of apneas, distinguish between central and obstructive apneas and provide an increased pressure if needed to stabilize an obstructed or partially obstructed airway.

Many stroke patients may be physically incapable of or experience discomfort in traveling to a sleep clinic for a sleep study. Hence there is a need to provide alternative methods and apparatus for treating the breathing disorders of stroke patients in rehabilitation. Furthermore, there are simply not enough places in sleep clinics to accommodate stroke patients. Thus in one aspect, the invention provides a simplified screening, diagnosis and treatment models suitable for patients in stroke rehabilitation which would not overburden the current sleep clinics.

Figure 1:
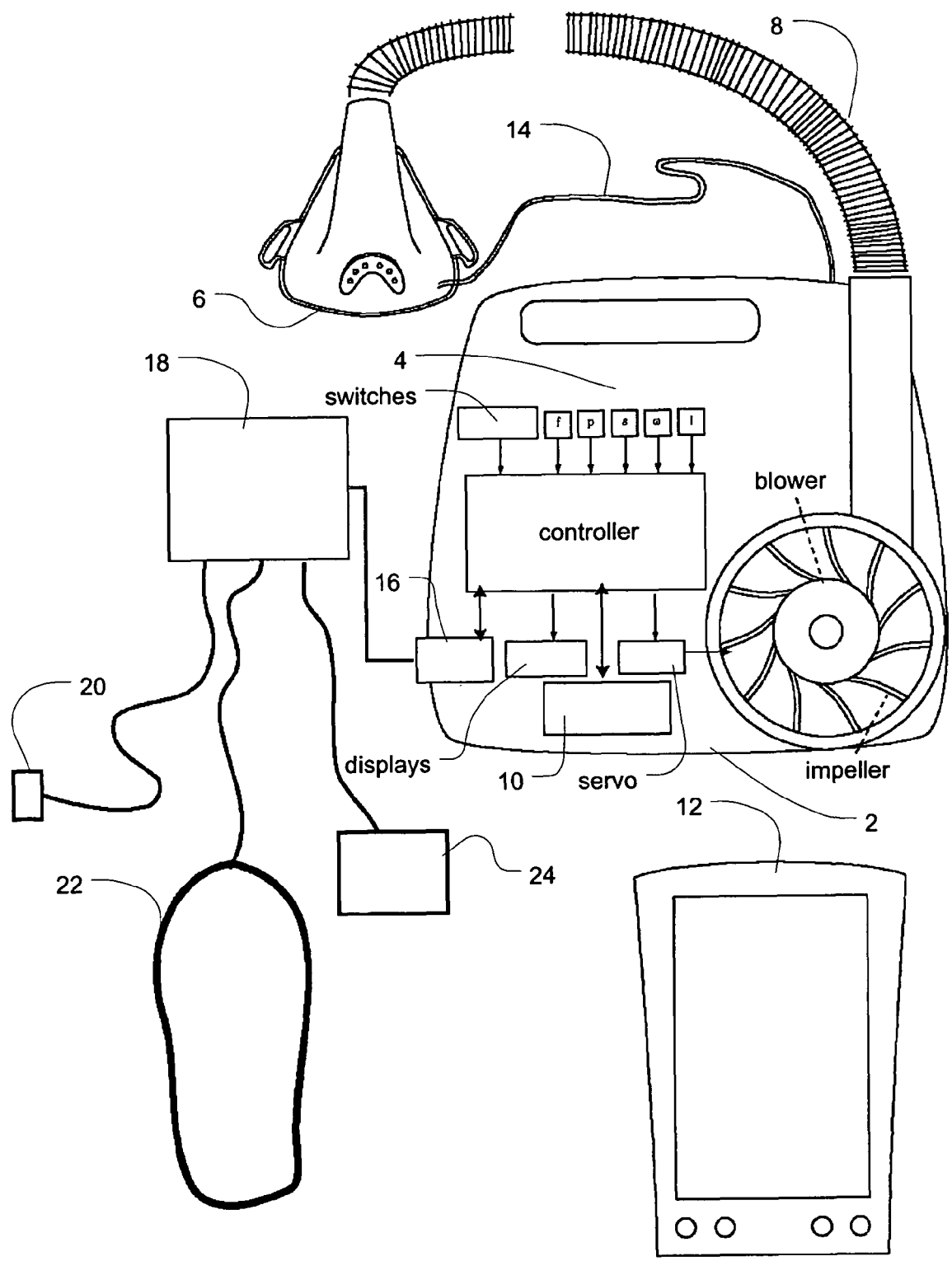
FIG. 1 shows apparatus according to the invention.

In reference to FIG. 1, the invention provides apparatus that includes a computer-controlled blower 2, flow and pressure sensors 4, a mask 6, air delivery conduit 8 for connection between the blower 2 and the mask 6. The apparatus further includes a communication port or module 10, for example, a wireless communication transceiver and/or a network card, for communication with other devices or computers such as hand-held display and control devices 12. The apparatus further includes an oximeter in the main blower housing. There is a sense tube 14 connected to the main housing of the blower to the mask which allows the apparatus to sense oxygen concentration and pressure levels in the mask 6. The apparatus further includes a communications interface 16 for connection to a diagnosis unit. The diagnosis unit includes a pulse oximeter 20, respiratory movement sensors 22, EEG & ECG 24.

While this apparatus is described as a single unit, it is understood that a combination of devices and/or computers linked by any available communications method may be used to accomplish the goals of the invention. For example, the apparatus can interface with a variety of hand-held devices such as a Palm Pilot via wireless communication. With such a device, a physician may, for example, remotely monitor, analyze or record the status or data history of a patient or diagnose the patient's condition using the device. For example, remote devices may store stroke indicators, such as in a database of patient stroke recovery information for one or more patients, from data generated by use of the apparatus. Furthermore, the treatment program which is being run on the patient can be monitored and changed remotely. In the event patient data is transmitted over open networks, the data may be encrypted for purposes of patient confidentiality.

The apparatus has two treatment modes, a first mode for treating obstructive apneas and a second mode for treating central apneas. In the first mode, the device provides a generally constant pressure throughout a breathing cycle, but may vary the pressure in accordance with indications of partial or complete obstruction of the airway. One technique for accomplishing this using a combination of flow limitation and snore measurements is described in U.S. Pat. No. 5,704,345 (Berthon-Jones). One apparatus embodying aspects of the invention described in the '345 patent is AUTOSET T™ (ResMed Ltd). Other known alternative methods to vary the pressure for delivering CPAP treatment to a patient to treat obstructive apneas would be recognized by those skilled in the art and may be utilized as modes in the device.

In one form of the second mode, the apparatus provides a higher pressure to the mask during the inspiratory portion of the breathing cycle, the so-called IPAP, and a lower pressure to the mask during the expiratory portion of the breathing cycle, the so-called EPAP. This may be accomplished by monitoring the respiratory flow to the patient and defining a threshold level. When flow exceeds the threshold then the device will deliver the IPAP, whilst below the threshold, the device will deliver the EPAP. The determination of respiratory airflow may be accomplished by monitoring the total flow rate of air to the patient and subtracting any components due to leak. Leak airflow may be determined by using a method such as taught in U.S. Pat. No. 6,152,129 (Berthon-Jones). Other known methods for determining leak may also be used by the device. The two different pressure levels may be achieved using a least two methods. In one method, a near-constant speed blower develops a constant pressure equivalent to the IPAP pressure and during the EPAP phase, some of the air is vented. In another method, a blower may be alternately accelerated and decelerated in order to develop the pressure appropriate for each phase of the breathing cycle. The VPAP™ II ST/A (ResMed Ltd) uses the latter method.

In another form of the second mode, the device delivers therapy in accordance with the methods taught in International Patent Application WO 99/61088 (Berthon-Jones)

The apparatus according to the invention may be used to monitor patient health characteristics including, for example, oral and/or nasal airflow, snore, abdominal movement, chest wall movement, oximetry, pulse rate, body position and flattening index via the diagnosis unit and sensors in the blower. As an alternative to the diagnosis unit apparatus according to the invention may be used in conjunction with a portable diagnosis system, for example, the EMBLETTA portable diagnosis system (FLAGA, Iceland), or the MESAM system (MAP, Germany). In a preferred embodiment, the flattening index is measured according to the method described in U.S. Pat. No. 5,704,345 (Berthon-Jones). The contents of U.S. Pat. No. 5,704,345 are hereby incorporated by cross-reference.

The apparatus generates one or several indices determined from an analysis of the patient's health characteristics useful for assessing appropriate treatment or diagnosing the condition of the patient. Such indices serve as stroke indicators to indicate patient improvement or stroke type as detailed below. An index determined in accordance with the invention may be used by a physician in conjunction with other known methods of analyzing the health of the patient. For example, an index in accordance with the invention may be used in conjunction with a cognitive test for assessing functional outcomes. In addition, an index in accordance with the invention may be used to assess a patient in conjunction with Magnetic Resonance Imaging (MRI). The apparatus may be used to monitor a patient and generate an index with or without applying a CPAP treatment regime.

One such index is based upon a functional relationship between the number of central or obstructive apneas over a particular time period. When the patient is being treated with CPAP, the device continuously monitors whether the patient is having an apnea and if so, whether the apnea is central or obstructive. The apparatus determines an index from a comparison of the number of central and obstructive apneas or a function of the ratio of the number of central to obstructive apneas during a particular time period.

Methods and apparatus for distinguishing between central and obstructive apneas are described in U.S. Pat. No. 5,704, 345. In one technique, when an apnea is detected as occurring, the apparatus applies an oscillatory pressure waveform of known frequency and magnitude and accesses the patency of the airway from the flow which is induced in the airway. In one form, if the airway is patent during an apnea, then the apnea is judged to be central. However, if the airway is closed during an apnea, then the apnea is judged to be obstructive. In another technique, when an apnea is detected as occurring, the apparatus monitors the airflow for the presence of a signal of cardiac origin. If a cardiac signal is detected, then the airway is judged to be patent and the apnea classified as central. If no cardiac signal is detected, then the airway is judged to be closed and the apnea classified as obstructive.

Other methods for distinguishing between central and obstructive apneas include monitoring chest movement using respiratory bands and monitoring the movement of the suprasternal notch, for example, as taught in International Patent Application WO 01/19433 (Berthon-Jones et al.).

This index may serve as an indication of the degree of neuro-recovery for a stroke patient. One effect of the stroke may be to damage those components of the brain which participate in respiratory drive, causing a relatively high incidence of central apneas compared to obstructive apneas. If neuro-recovery causes the patient to recover some of that respiratory drive, there would be an impact on the index when compared to an index recorded closer in time to the occurrence of stroke.

Alternatively, the effect of the stroke may be to damage brain tissue involved in the autonomic nervous system, which may cause a loss of muscle tone, for example to the airway. In turn this may lead to a relatively higher incidence of obstructive apneas. Hence the index may be used as part of the assessment techniques to determine the type of stroke which the patient has suffered. Use of the index may assist in assessing the location of the stroke, and in determining the appropriate form of therapy.

The changing value of the index may also provide an indication to the physician that the dosage of pharmacological agents given to the patient ought to be changed. For example, if the index indicated that neuro-recovery was occurring, then it may be appropriate to reduce the dose of the agent. Alternatively, the index may be used to monitor the efficacy or effectiveness of a drug protocol. For example, by monitoring the index for one or more patients, which may include the storing of multiple indices in a database of patient information, and by an analysis of such data, it may be determined that a drug is safe and/or appropriate as a treatment for stroke in general. Additionally, monitoring and analysis may indicate that a particular treatment is working for a particular patient.

The index may also be used as part of a CPAP-device management strategy. If a patient is being treated with a relatively more expensive computer controlled CPAP device that is capable of treating both obstructive and central apneas, yet the index indicates that the patient has few central apneas, then it may be appropriate to treat the patient with a relatively cheaper basic CPAP device which does not distinguish between central and obstructive apneas.

An additional index may be a function of the pressure delivered to the patient. In a computer controlled CPAP device such as ResMed Ltd.'s AUTOSET T™ which can automatically increase the CPAP pressure during an obstructive apnea to stabilize the airway, a record of the pressures used to treat the patient may provide an indication of the changing status of the patient. For example, monitoring the 95th percentile of pressure delivered during the previous treatment session, as described in International Patent Application PCT/AU99/01130, may provide such a status indication. Furthermore, an history of the 95th percentile of the previous treatment session kept over several months may provide an index of stroke recovery.

Neuro-recovery may result in an increase in upper airway muscle tone which in turn leads to a decrease in the CPAP pressure needed to treat an obstructive apnea. Monitoring the 95th percentile may be useful as part of a CPAP-device management strategy. For example, if a patient is being treated with a relatively more expensive computer controlled CPAP device, yet the 95th percentile index indicates that there is little change in the pressure being delivered, it may be appropriate that the patient be treated with a relatively cheaper basic CPAP device which delivers a fixed pressure.

Another index is an Apnea Hypopnea Index ("AHI") which is an indicator of the level of severity of a patient's sleep disordered breathing. The AHI is determined by adding the total number of apneas and hypopneas the patient experienced over a particular time period, such as during the study, and dividing that figure by the total time for that period. An example of an AHI scoring rule set is: (i) An apnea is scored if the 2-second moving average ventilation drops below 25% of the recent average (time constant=100 s) for at least 10 consecutive seconds. (ii) An hypopnea is scored if the 8 second moving average drops below 50% but not more than 25% of the recent average for 10 consecutive seconds. Other forms of AHI index are known by those skilled in the art.

The described apparatus may be used for the treatment and diagnosis of stroke victims in accordance with the following protocol or programmed to follow a decision making protocol to provide automated assistance in the process of evaluating the condition of and identifying appropriate treatment for patients after stroke. A single device or multiple devices may be used to accomplish this protocol.

Patients typically enter rehabilitation clinics as a "stepping stone" between an acute care ward in a hospital and a return to normal community life. The patients may come from stroke units, spinal units, respiratory wards or a number of other wards. Upon admission to a rehabilitation clinic, the physician can conduct a sleep history assessment of the patient with the questionnaire appearing on the hand-held device and the results being sent to the apparatus. In conjunction with the assessment, the apparatus then may recommend particular further tests to be done, such as oxygen saturation, and overnight sleep studies. The apparatus can conduct these tests and recommend treatment levels. Further, the apparatus can provide CPAP treatment.

There are a number of different patient treatment models which are shown as flowcharts in FIG. 2 to 6. The flow charts, and later discussion, indicate AutoSet T and VPAP as particular embodiments of the invention, however it is to be noted that in other forms of the invention, other forms of CPAP and bi-level CPAP may be used. As part of the patient treatment model, the apparatus can provide the physician with the appropriate healthcare reimbursement scheme codes.

Figure 2:
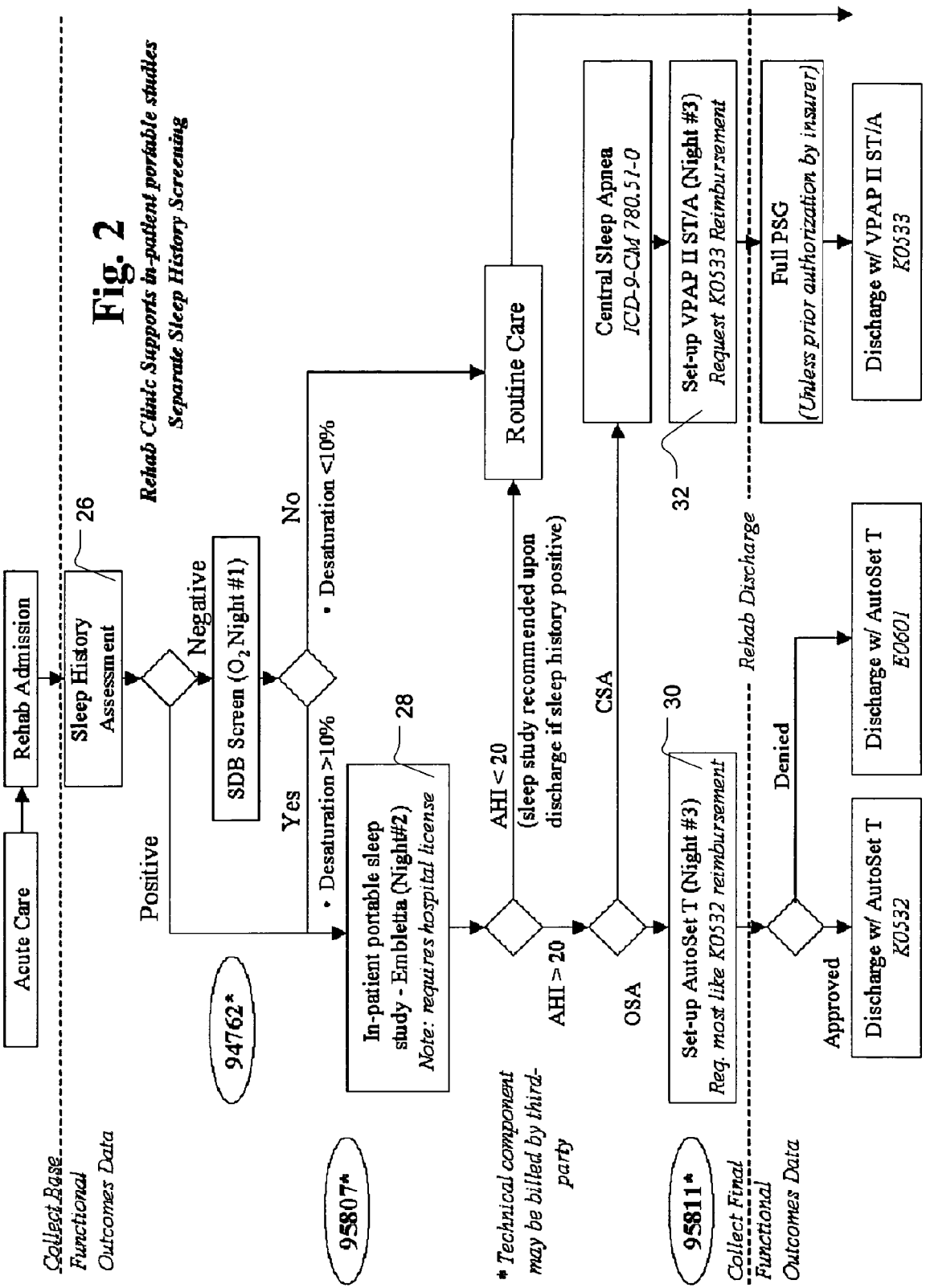
FIG. 2 shows a first in-patient flowchart according to the invention.

In the first model, shown in FIG. 2, patients pass from acute care to rehabilitation admission. According to the invention, all patients entering the rehabilitation clinic are asked a number of simple questions in a Sleep History Assessment, step 26, which are designed to probe for the possibility of sleep disorders.

A set of possible questions is as follows:
Do you suffer from excessive daytime sleepiness?
Do you suffer from nocturnal choking?
Do you have restless sleep?
Do you snore? or Has anyone told you that you snore?
Do you stop breathing during sleep or has anyone ever told you that you stop breathing during sleep ?
Do you suffer from a dry throat in the morning?
Do you suffer from headaches in the morning?
Do you feel very tired during the day?
Do you feel very sleepy during the day?
Have you ever fallen asleep while driving?

These questions are suitable for flagging the possibility that a patient be given a more rigorous and detailed assessment by a trained sleep or respiratory physician. A positive determination indicates that an in-patient sleep study should be conducted.

During one form of sleep study such as by a portable device, the patient's breathing is monitored. Their Apnea Hypopnea Index (AHI) is determined and each event is classified. Apneas can be classified as obstructive, central or mixed. Other events which can be identified include hypopneas, snoring & partial upper airway obstruction. Effort, position, oxygen saturation and flow limitation index can also be determined.

During a night of testing, step 28, patients with an Apnea Hypopnea Index (AHI) of greater than a threshold of about 20 are assessed to determine if they have Central Sleep Apnea (CSA) or OSA. During a central apnea, patients provide no respiratory effort. During an obstructive apnea, the patient's effort is obstructed by, for example, an overly flexible upper airway which physically blocks their attempts at breathing. A patient may have both central and obstructive apneas on different occasions. Those with OSA are given a night's assessment with an AUTOSET T™ apparatus to determine if treatment with that particular device is appropriate for the patient, step 30. This assessment is based upon accepted medical standards for the use of the device. If this assessment results in approval, the patient will be sent home with an AUTOSET T™ apparatus. Those patients diagnosed with CSA are assessed with a bi-level CPAP device, step 32, such as the ResMed VPAP II ST/A. They are also given full polysomnography (PSG).

Patients with a negative result from the sleep history assessment are given a night's oxygenation screening using the apparatus. Those patients indicating a greater than 10% desaturation are given an in-patient portable sleep study as described above. Those patients indicating a less than 10% desaturation are recommended routine care.

Figure 3:
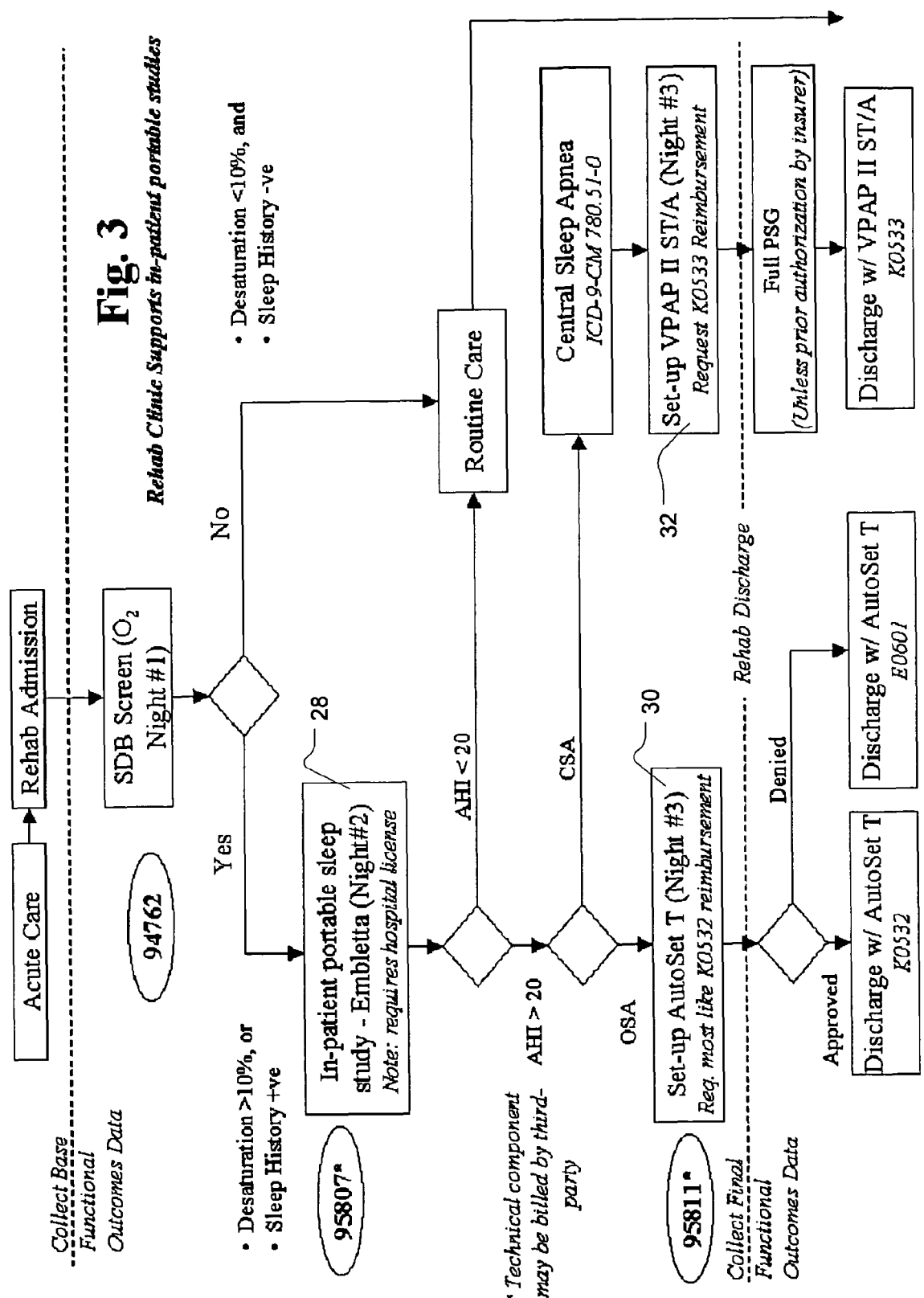
FIG. 3 shows a second in-patient flowchart according to the invention.
Figure 4:
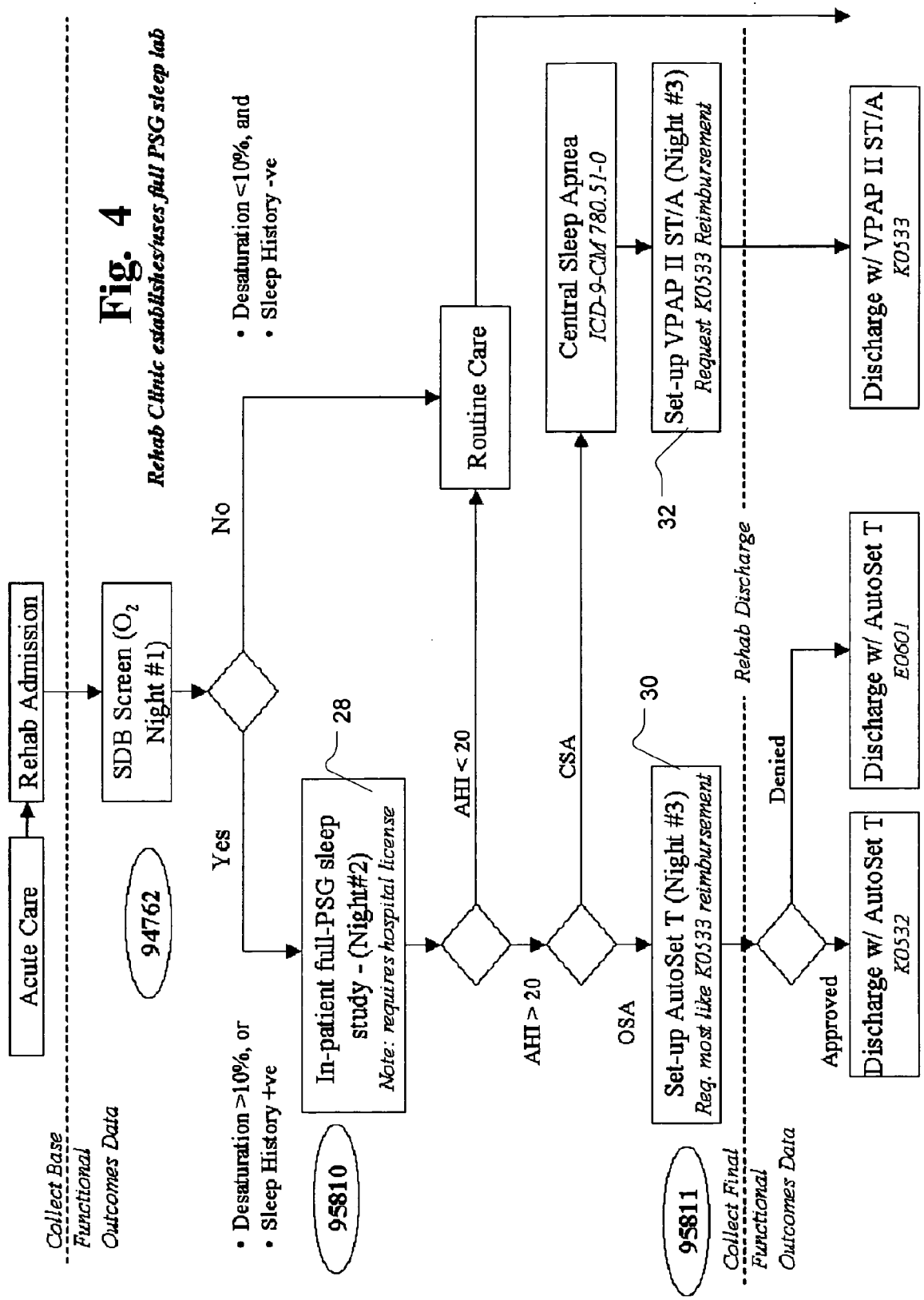
FIG. 4 shows a third in-patient flowchart according to the invention.

According to the clinical path shown in FIG. 3, the patient does not undergo sleep history assessment, otherwise, the path is similar to FIG. 2. According to the clinical path shown in FIG. 4, patients diagnosed with Central Sleep Apnea do not undergo full polysomnography, otherwise the path is similar to FIG. 3.

Figure 5:
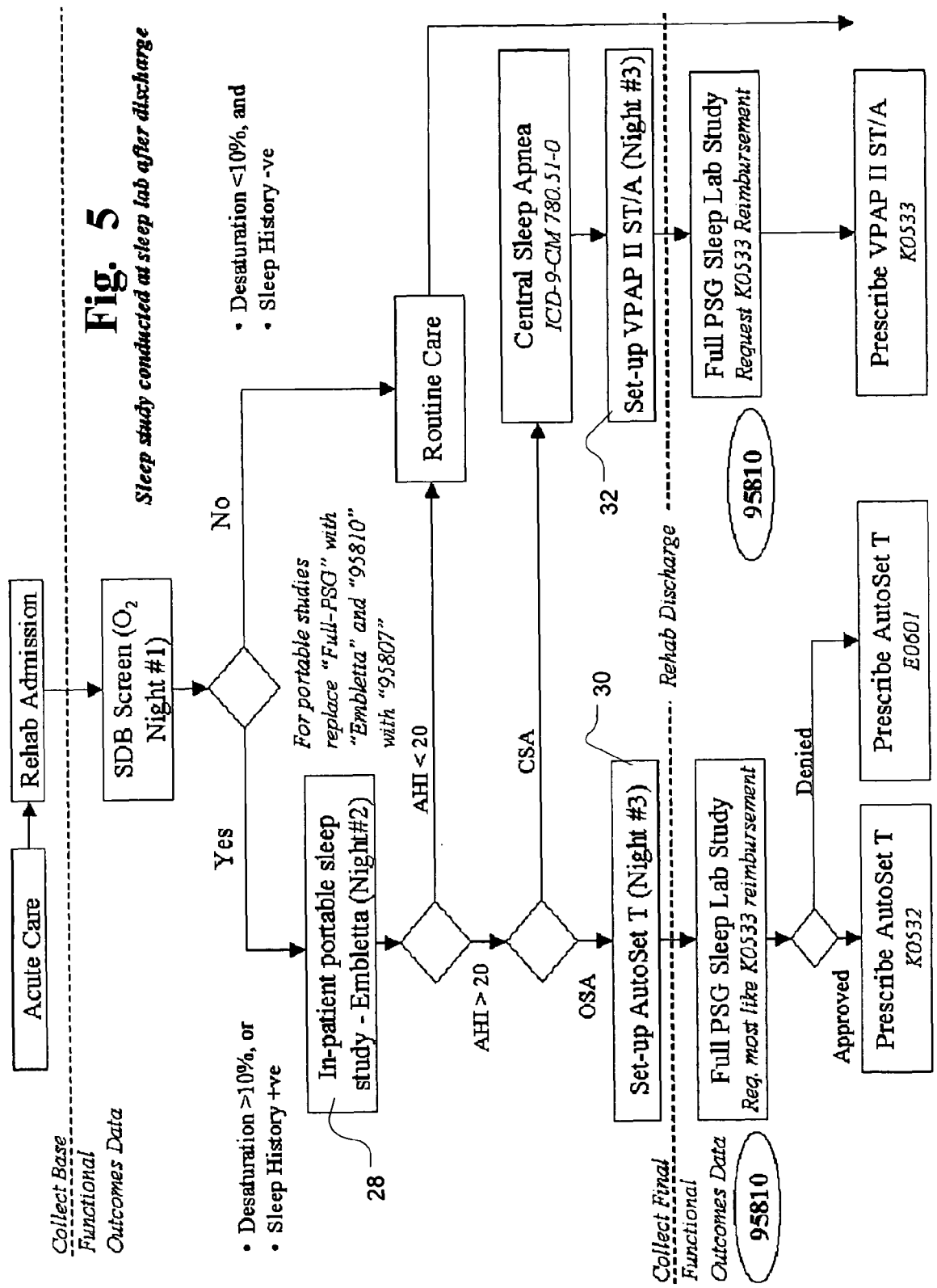
FIG. 5 shows a first out-patient flowchart according to the invention.
Figure 6:
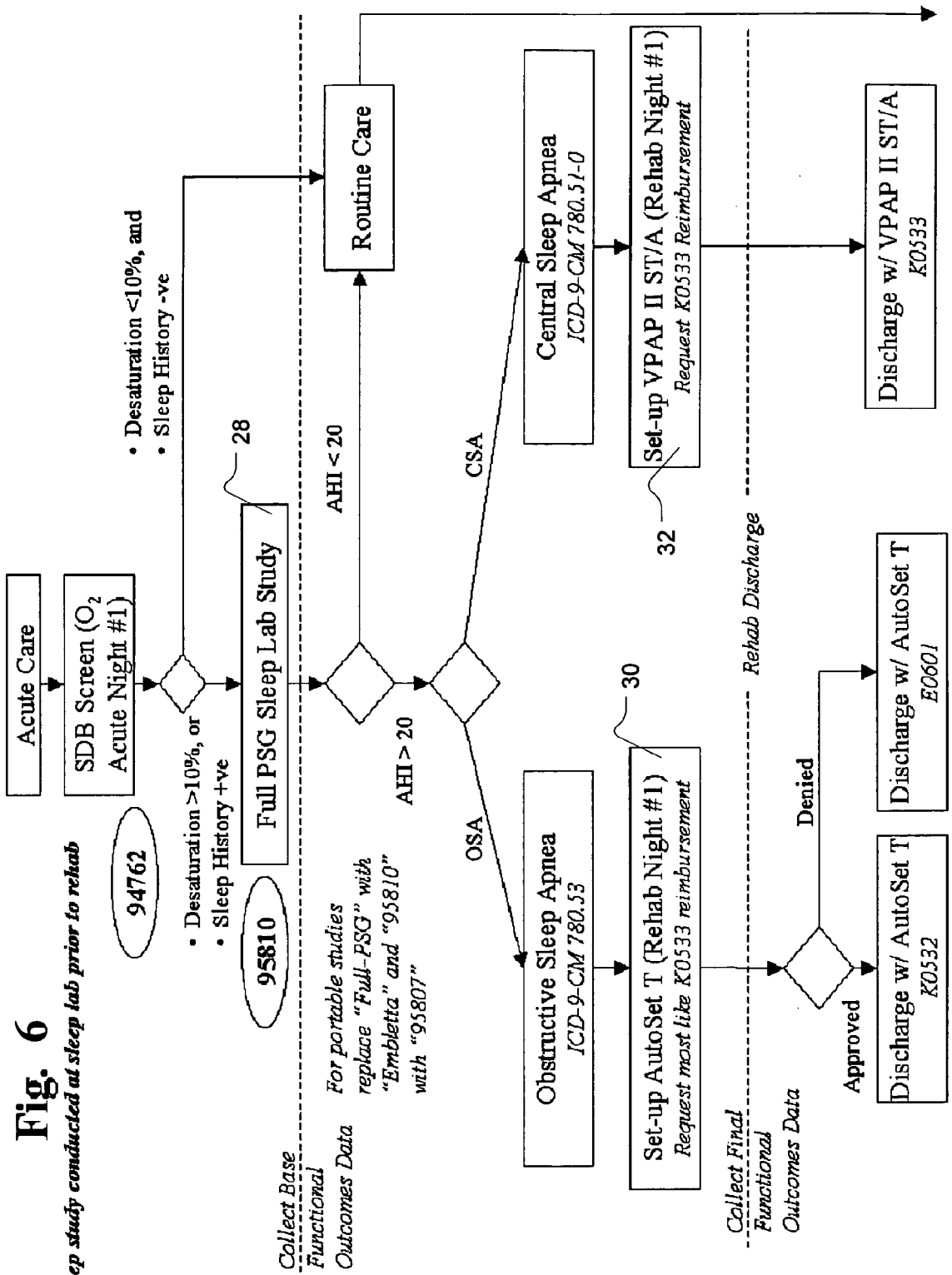
FIG. 6 shows a second out-patient flowchart according to the invention.

The first out-patient clinical pathway is conducted in a sleep laboratory after discharge from a rehabilitation hospital. As shown in FIG. 5, the patient is screened for Sleep Disordered Breathing (SDB) by measuring blood oxygenation overnight using apparatus according to the invention. Those patients with a desaturation of less than 10% and a negative sleep history proceed to routine care. Those patients with either a positive sleep history (for example, as determined via the questioning indicated above) or a desaturation of greater than 10% proceed to a night study using the apparatus or alternatively, a portable device such as the EMBLETTA as described above.

Those patients with an AHI of less than a threshold of about 20 proceed to routine care. Those patients with an AHI of greater than about 20 are assessed to determine whether they have CSA or OSA. Those with OSA are assessed overnight with an AUTOSET T™ apparatus and full polysomnography after which they may be prescribed to take home the AUTOSET T™ apparatus. Those patients with CSA are assessed with a VPAP apparatus and full polysomnography. They may then be prescribed with a VPAP apparatus. While the invention discloses 20 as a threshold, by recording stroke indicators such as the AHI of many patients in a database and analyzing other data for the patients, the threshold may be adjusted to improve the accuracy of the threshold.

A second clinical pathway for out-patients is conducted in a sleep laboratory prior to entry to a rehabilitation hospital. During the first night, the patient is screened for SDB using an oximeter. Those patients with a desaturation of less than 10% and a negative sleep history pass to routine care. Those patients with a greater than 10% desaturation or a positive sleep history indicating the possible presence of SDB then pass to a night's full polysomnography. Those with an AHI of less than 20 pass to routine care. Those with an AHI of greater than 20 are assessed to determine if they experience CSA or OSA. Those with CSA are assessed with a VPAP™ apparatus and may be discharged with the device. Those with OSA are assessed with an AUTOSET T™ apparatus and may be discharged with the device.

Another aspect of the invention is that there is a follow-up for OSA patients of approximately 4 weeks after treatment using the AUTOSET T™ apparatus. This period allows the patient to become more familiar with wearing the mask and breathing against the pressure. Importantly, since in the AUTOSET T™ apparatus the device monitors patient compliance, the efficacy of treatment can be assessed. For example, the number hours of patient treatment including actual hours when the device was used and not simply switched on can be reviewed by the clinic.

In a preferred embodiment, the apparatus identifies, displays and/or records reimbursement codes relating to the treatment provided by the apparatus. For example, the apparatus may be programmed to provide the appropriate US Medicare reimbursement codes indicated in FIG. 2 to the physician via a hand-held device or other centralized computer to assist in the process of applying for funding of the treatment.

The Medicare codes which are provided for physician information by the apparatus, as shown on FIG. 2 to 6 are now described in more detail. ICD-9-CM coding is recommended for all clinical settings and is required for reporting disease and diagnosis to all US public health services and HCFA programs. A physician needs to select the CPT code and descriptor that most accurately identifies the procedure or service performed, and it may be provided by the apparatus. The physician may also list additional procedures performed or pertinent special services and when necessary, any modifier. All procedures and services need to be accurately documented in the patient's medical record, which may be accomplished through the communications module. The code may be subject to a modifier. A modifier enables the reporting physician to indicate that a performed service has been altered by some circumstance. Modifiers may be used to indicate: (a) a technical-only or professional-only component of services or procedures (e.g., 95810 TC indicates the technical-only component of a sleep study) and (b) that a service or procedure was performed in part (e.g., 95810-52 indicates a sleep study with a reduced number of channels recorded). Level I modifiers are used in conjunction with Level I codes (CPT codes). When billing CPT Code 95805, 95806, 95807, 95808, 95810, or 95811, an ICD-9-CM code must be used.

FIG. 7 depicts an in-patient protocol in accordance with an embodiment of the invention. In accordance with the embodiment depicted in FIG. 7, a patient enters rehabilitation hospital in step 71. In step 72, a sleep disordered breathing (SDB) questionnaire such as the one described above is given to the patient. The results of the questionnaire are reviewed by a physician in step 73. If the questionnaire provides a negative assessment of SDB, and there is no suspicion of SDB, no further assessment of the patient takes place, as indicated in step 74. However, if the assessment indicates that there is a suspicion of SDB, further assessment is carried out, as indicated in step 77. In one form of assessment, a portable diagnostic system, such as Embletta (Flaga, Iceland) is used as indicated by step 79(*a*). In another form of assessment, full polysomnography (PSG) is carried out on the patient, as indicated in step 79(*b*). If either the portable or full diagnosis steps provides a negative result, as indicated in steps 78 and 80 respectively, no further assessment of the patient is carried out. Following the flowchart line from the portable diagnostic system, if there is a positive outcome from the assessment, (step 81) a trial of an automatically titrating CPAP device, such as AutoSet T, is provided as indicated in step 83. This is given a review at four weeks, as indicated in step 86. If the SDB is resolved, treatment with the automatically titrating CPAP device is discontinued. If the SDB does not resolve, treatment with a fixed pressure CPAP or an automatically titrating CPAP device is continued as indicated in step 89. In addition, in step 90, the patient is followed up in a CPAP clinic as appropriate. Following the flowchart line from a positive full polysomnography, a full CPAP titration study is carried out in step 85. A patient may then go on to a fixed pressure CPAP or an automatically titrating CPAP, such as AutoSet T. In common with the flowchart path from a portable diagnostic system, a patient following the full PSG diagnosis will be followed up in a CPAP clinic as appropriate. Steps 79 to 90 may be managed by a sleep service facility.

While the invention has been described in one form, it is to be understood that this form is merely illustrative of the invention. For example, it is contemplated that a device in accordance with an embodiment of the invention conducts monitoring during a monitoring period of a patient without delivering air at positive pressure. In this embodiment, a device may include an airflow monitor, such as an airflow sensor, a respiratory effort monitor, such as a respiratory band or suprasternal notch sensor, and a computer programmed to calculate the number of central and obstructive apneas from data from the airflow and respiratory effort monitors and derive a stroke indicator therefrom. Those skilled in the art would understand that the stroke indicator may be calculated using data from the monitoring period. Furthermore, the stroke indicator may be calculated at a location remote from the monitoring device. Other variations can be made without departing with the spirit and scope of the invention.

The invention claimed is:

1. A method for evaluating the condition of a patient after stroke comprising the steps of:
   delivering breathable gas at a pressure above atmospheric to a patient after stroke;
   measuring the airflow of said patient; and
   determining, using a computer, a stroke indicator from said airflow, said stroke indicator representing information about the patient's stroke condition.

2. The method of claim 1 wherein said determining step includes analyzing said airflow to determine an occurrence of central apnea and said stroke indicator is calculated as a function of said occurrence of central apnea.

3. The method of claim 2 wherein said determining step includes analyzing said airflow to determine an occurrence of obstructive apnea and said stroke indicator is calculated as a function of said occurrence of obstructive apnea.

4. The method of claim 1 further comprising the step of evaluating changes in said stroke indicator to assess the efficacy of an administered drug.

5. The method of claim 4 wherein said step of evaluating said stroke indicator includes storing said stroke indicator in a database of patient information.

6. The method of claim 5 wherein said stroke indicator is a function of a number of occurrences of central apnea.

7. The method of claim 6 wherein said stroke indicator is a function of a number of occurrences of obstructive apnea.

8. A method for evaluating the condition of a patient after stroke in accordance with claim 1 further comprising the steps of:
   determining the number of central and obstructive apneas which the patient has during a first time period; and
   calculating a stroke indicator index from a comparison of the number of central and obstructive apneas which the patient has during the first time period, said stroke indicator representing information about the patient's rehabilitation from stroke.

9. An apparatus for evaluating the condition of a patient after stroke comprising:
   a source for delivering breathable gas at a pressure above atmospheric to a patient after stroke;
   a sensor for measuring the airflow of said patient; and
   means for determining a stroke indicator from said airflow, said stroke indicator representing information about the patient's stroke condition.

10. An apparatus for evaluating the condition of a patient after stroke in accordance with claim 9 wherein said determining means analyzes said airflow to determine occurrences of central apneas and said stroke indicator is determined as a function of said occurrences of central apneas.

11. An apparatus for evaluating the condition of a patient after stroke in accordance with claim 10 wherein said determining means analyzes said airflow to determine occurrences of obstructive apneas and said stroke indicator is determined as a function of said occurrences of obstructive apneas.

12. An apparatus for evaluating the condition of a patient after stroke in accordance with claim 9 wherein said determining means further evaluates changes in said stroke indicator to assess the efficacy of an administered drug.

13. An apparatus for evaluating the condition of a patient after stroke in accordance with claim 12 wherein said determining means further stores the evaluated stroke indicator in a database of patient information.

14. An apparatus for evaluating the condition of a patient after stroke in accordance with claim 13 wherein said stroke indicator is evaluated as a function of a number of occurrences of central apneas.

15. An apparatus for evaluating the condition of a patient after stroke in accordance with claim 14 wherein said stroke indicator is evaluated as a function of a number of occurrences of obstructive apneas.

16. An apparatus for evaluating the condition of a patient after stroke in accordance with claim 9 further comprising
   effort sensor means for measuring the respiratory effort of the patient;
   and wherein said determining means monitors the airflow and effort sensor means to determine a number of central and obstructive apneas which the patient has during a first time period, and calculates said stroke indicator from a comparison of the number of central and obstructive apneas which the patient has during the first time period, said stroke indicator representing information about the patient's recovery from stroke.

17. The apparatus for evaluating the condition of a patient after stroke in accordance with claim 16 wherein the effort sensor means is a respiratory band.

* * * * *